United States Patent [19]
Zaffaroni

[11] 3,948,262

[45] *Apr. 6, 1976

[54] NOVEL DRUG DELIVERY DEVICE

[75] Inventor: Alejandro Zaffaroni, Atherton, Calif.

[73] Assignee: Alza Corporation, Palo Alto, Calif.

[ * ] Notice: The portion of the term of this patent subsequent to July 29, 1992, has been disclaimed.

[22] Filed: Mar. 10, 1975

[21] Appl. No.: 556,546

Related U.S. Application Data

[60] Division of Ser. No. 185,208, Sept. 30, 1971, Pat. No. 3,896,819, which is a continuation-in-part of Ser. No. 42,786, June 2, 1970, Pat. No. 3,854,480, which is a continuation-in-part of Ser. Nos. 812,116, April 1, 1969, Pat. No. 3,598,122, and Ser. No. 864,175, Oct. 6, 1969, abandoned.

[52] U.S. Cl. .............. 128/260; 128/268; 128/270; 128/272; 128/285; 424/20; 128/130
[51] Int. Cl.² .... A61F 5/46; A61M 7/00; A61J 1/00
[58] Field of Search .......... 128/260, 263, 268, 270, 128/272, 285, 284, 130

[56] References Cited
UNITED STATES PATENTS

| | | | |
|---|---|---|---|
| 3,279,996 | 10/1966 | Long, Jr. et al. .............. | 128/272 X |
| 3,598,115 | 8/1971 | Horne, Jr. ............................ | 128/130 |
| 3,705,938 | 12/1972 | Hyman ............................ | 128/260 X |
| 3,710,795 | 1/1973 | Higuchi et al. ...................... | 128/260 |

OTHER PUBLICATIONS
Kincl, et al., "Sustained Release Hormonal Preparations," Steroids, Vol. 11, No. 5, May 1968, pp. 673–680.
Chang, et al., "Sustained Release Hormonal Preparations," Fertility and Sterility, Vol. 21, No. 2, Feb. 1970, pp. 134–139.
Unknown, "An Unusually Effective IUD Device That Has 'No Systemic Effects'", Medical World News, May 25, 1973, pp. 55–56.
Kratochvil, et al., "Sustained Release Hormonal Preparations," Steroids, Vol. 15, No. 4, Apr. 1970, pp. 505–511.

*Primary Examiner*—Aldrich F. Medbery
*Attorney, Agent, or Firm*—Thomas E. Ciotti; Paul L. Sabatine; Edward L. Mandell

[57] ABSTRACT

A drug delivery device for administering a drug at a controlled rate for a prolonged period of time to produce a local or systemic physiological or pharmacological effect is comprised of a wall surrounding a reservoir containing a drug. The reservoir is formed of a drug carrier permeable to the passage of the drug and in which the drug has limited solubility. The wall is formed in at least a part of a drug release rate controlling material also permeable to the passage of the drug, but the rate of passage of the drug through the wall is lower than the rate passage of the drug through the drug carrier so that drug release by the wall is the drug release rate controlling step for releasing drug from the drug delivery device.

20 Claims, 8 Drawing Figures

NOVEL DRUG DELIVERY DEVICE

This is a divisional application of copending application Ser. No. 185,208 now U.S. Pat. No. 3,896,819, filed Sept. 30, 1971, which in turn is a continuation-in-part of application Ser. No. 42,786, filed June 2, 1970, now U.S. Pat. No. 3,854,480, which in turn is a continuation-in-part of application Ser. No. 812,116, filed Apr. 1, 1969, now U.S. Pat. No. 3,598,122 and application Ser. No. 864,175, filed Oct. 6, 1969, now abandoned.

BACKGROUND OF THE INVENTION

This invention relates to a novel and useful drug delivery device for releasing drug at a controlled rate for a prolonged period of time to produce a local or systemic physiological or pharmacological effect. The drug delivery device is comprised of a reservoir surrounded by a wall. The reservoir is comprised of a drug within a carrier permeable to the passage of the drug and in which the drug has limited solubility. The wall of the device is comprised in at least a part of a drug release rate controlling material permeable to the passage of the drug. Both the carrier and the wall are permeable to the passage of drug, as by diffusion, but the permeability of the wall to the drug is lower than the permeability of the carrier to the drug. Accordingly, drug release through the wall is the drug release rate controlling step for releasing drug from the drug delivery device of the invention.

The terms and phrases such as "reservoir", "carrier", "drug", "limited solubility", and the like that appear throughout the specification and accompanying claims are defined in the specification in the section entitled, "Detailed Description of the Invention."

In many therapeutic programs pertaining to the management of health and disease, it is desirable and indicated to use a drug delivery device to provide for the slow release of a drug to the body at a controlled rate over a prolonged period of time to achieve a desired physiologic or pharmacologic effect. In many instances, such a rate of release of the drug from a drug delivery device should have a zero order time dependence, that is, the rate of drug release is independent of time.

Different approaches have been tried by the prior art to obtain such a drug delivery device. One approach, which has received great attention, is to mix a drug with a carrier material that is gradually broken down by body fluids with the drug released as the carrier disintegrates. Numerous carriers have been used in such devices including waxes, oils, fats, soluble polymers, and the like. While some of these devices have provided for a delayed release of the drug, the desired constant release rate for a prolonged period has not been obtained. One reason for this is that as the carrier disintegrates the surface area of the dosage unit decreases, concomitantly exposing increasingly smaller quantities of the carrier to the surrounding body fluids. This inherently results in a decline in the release rate over time.

Another approach to this problem has been to disperse the drug throughout a solid matrix material through which the desired amount of the drug is released by diffusion. But, this type of drug delivery device has proven incapable of providing a zero order drug release rate, because of the drawback that the release rate $(dM_t/dt)$ instead of being zero order $(dM_t/dt = \text{constant})$ decreases with time $(dM_t/dt = \text{constant} \times t^{-1/2})$ during much of the drug release history; J. Pharm. Sci., Vol. 52, pages 1145 to 1149, 1963.

Still another approach has been to enclose the drug within a single capsule having a polymeric wall or walls through which the drug can pass, for example, by diffusion. An approach of this kind is set forth in U.S. Pat. No. 3,279,996. These devices too, have inherent difficulties. One difficulty encountered is that small devices containing a small amount of dry, powdered drug are hard to fabricate because the device can be manufactured from only a few materials and further because the materials having the drug must be non-toxic as they contact the body. Additionally, these prior art devices have generally been based on the use of a single material, such as silicone rubber polymers, especially polydimethylsiloxane, as the diffusion control membrane. In large part, these polymers were selected because of their permeability to some important drug molecules. But, it has been found that mere high permeability without consideration of release rate controlling properties can be a significant disadvantage which defeats the primary object of an acceptable drug delivery device. Thus, with many important drug molecules, such as progesterone, the diffusion rate through a polydimethylsiloxane membrane is very great, and it is often greater than the rate of clearance of the diffused drug from the outer surface of the capsule. In many instances this results in the rate limiting step being clearance of the drug from the exterior of the capsule, rather than diffusion through the capsule wall. Clearance rate within the body is difficult to control, as it is subject to frequent change, and this inherently defeats the objects of providing a drug delivery device which releases drug at a constant rate over prolonged time.

In my copending application, U.S. Ser. No. 42,786 filed June 2, 1970, and assigned to the assignee of this invention, there is described a drug delivery device comprised of a drug dispersed in a solid matrix permeable to passage of the drug and surrounded by a membrane, also permeable to passage of the drug but at a lower rate than through the matrix. That device has proven itself capable of zero order drug release and represents a substantial improvement over previously proposed drug delivery devices. However, in some instances, when zero order drug release is required for long periods of time, on the order of several months to a year or more, it may not be attained with the device of that copending patent application. Thus, it has been found that as drug is released by that device there is created over time a space in the solid matrix drug carrier which if not occupied by more drug can result in the carrier contracting and moving away from the membrane. The loss of contact between the carrier and the membrane at the carrier/membrane interface tends to decrease the availability of drug at the interface for release by the membrane. Thus, since the amount of drug available to the membrane is no longer constant, drug is released from the device at a continually reduced rate and the device does not maintain a constant zero order release rate. For applications in which controlled release is demanded for very long periods, this can be a problem.

It is also known to the art to incorporate drug into certain types of liquid carriers, usually in microcapsule formulations, for example, U.S. Pat. No. 3,464,413. However, these microcapsules are not designed for the controlled release of drug for a prolonged period of time by using drug release rate controlling materials. The microcapsules are frequently crushable, and they merely function as drug carriers supplying their drug in bulk, and not in controlled amounts by rupture of the microcapsules. Therefore, these types of capsules are not suitable for releasing drug at a controlled rate for a prolonged period of time.

SUMMARY OF THE INVENTION

Accordingly, it is an immediate object of this invention to provide a drug delivery device for the administration of locally acting or systemically acting drugs to produce a physiologic or pharmacologic effect which device overcomes the aforesaid disadvantages associated with the prior art modes of administration devices.

Still another important object of the invention is to provide a drug delivery device for releasing drug at a controlled rate for a prolonged period of time.

Yet still another object of this invention is to provide a drug delivery device which can release drug at a rate which does not vary with time.

Still yet another object of the invention is to provide a reliable and easily used drug delivery device for continuously administering controlled quantities of drug to the body or to drug receptor sites.

A further object of this invention is to provide a complete dosage regimen for a particular time period, the use of which requires intervention only for initiation and termination of the regimen.

In accomplishing these objects and advantages of this invention, one feature of the invention, in its broadest aspect, resides in a novel drug delivery device comprising a wall enclosing a reservoir. The reservoir is comprised of a drug within a liquid carrier permeable to the passage of the drug, as by diffusion, and having limited solubility for the drug. The wall surrounding the reservoir is comprised in at least a part of a drug release rate controlling material permeable to the passage of the drug, as by diffusion, but at a lower rate than through the liquid carrier. The wall is supplied with drug by passage of drug from the carrier. Drug entering the drug release rate controlling material comprising the wall passes therethrough for administration to the body or to a drug receptor site. Since the permeability of the carrier to the drug is always higher than the permeability of the drug release rate controlling material, the passage of drug through the wall is the rate determining step for drug release from the drug delivery device.

Other objects, features, and advantages of the invention will be apparent to those skilled in the art from the detailed description of the invention which follows, taken in conjunction with the drawings, and the accompanying claims.

BRIEF DESCRIPTION OF THE DRAWINGS

In the drawings, which are not drawn to scale, but rather are set forth to illustrate various embodiments of the invention, the drawings are as follows.

In the drawings and specification, like parts in related figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 1:
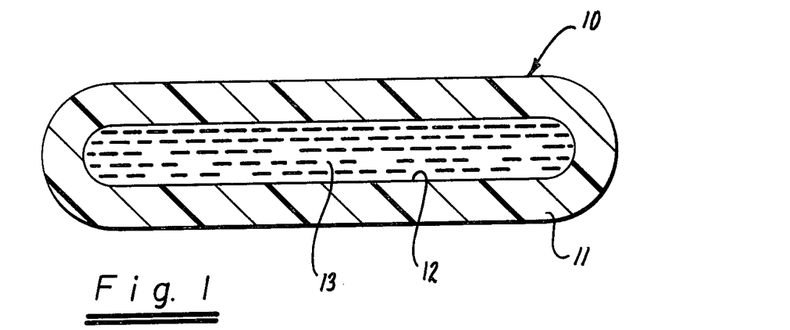
FIG. 1 is a perspective, cross-sectional view of a drug delivery device of the invention depicting a wall surrounding a reservoir.
Figures 2, 3, 4:
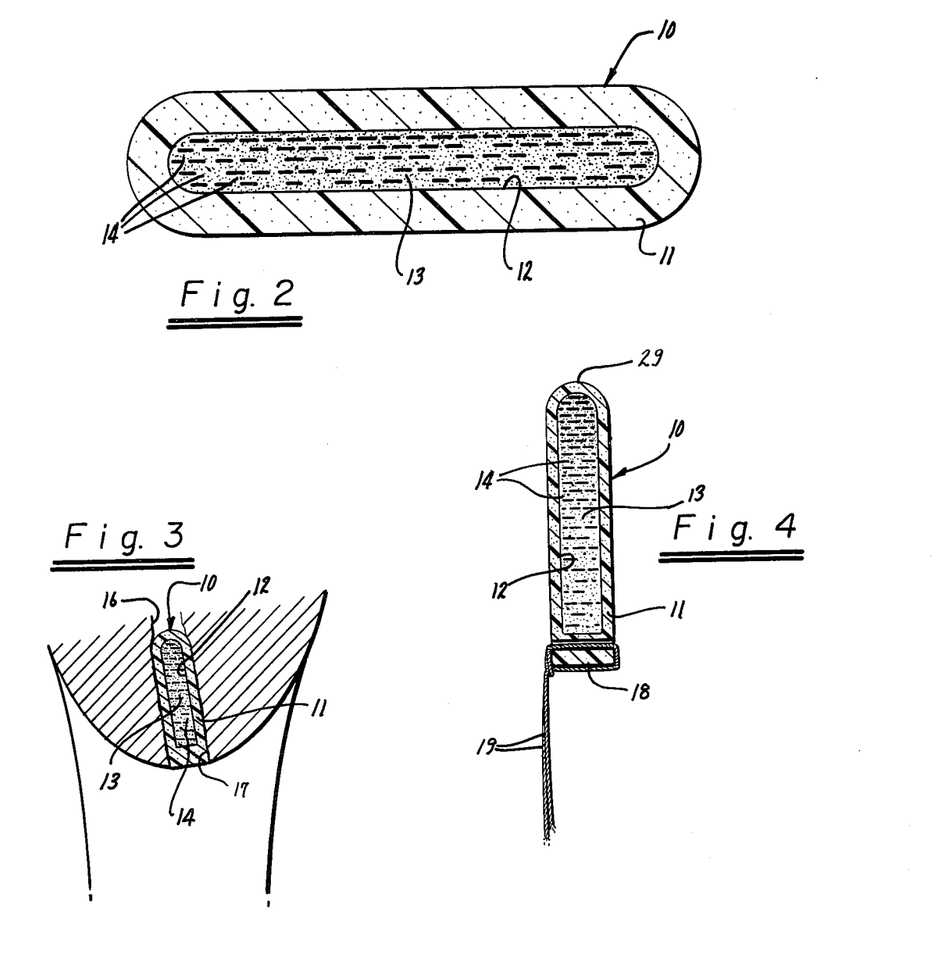
FIG. 2 is a cross-sectional view of the drug delivery device of FIG. 1 depicting drug contained in the reservoir.
FIG. 3 is a side, fragmentary view depicting an anal drug delivery device of the invention for releasing drug in a body orifice.
FIG. 4 is an elevational view of a drug delivery tampon embodying the principles of the invention.

Turning now to the drawings in detail, which are examples of various drug delivery devices of the invention, and which examples are not to be construed as limiting, one embodiment of a novel drug delivery device is indicated in FIGS. 1 and 2 by the number 10. Drug delivery device 10 is comprised of a wall 11 surrounding a reservoir 12. Reservoir 12 is comprised of a drug carrier 13 as shown in both FIGS. 1 and 2 and as further shown in FIG. 2 drug carrier 13 contains a drug 14, or a mixture of drugs. Drug carrier 13 is a liquid carrier, a description of which is presented later in the disclosure and it is permeable to the passage of drug 14, as by diffusion or by convection. Additionally, another important aspect of drug carrier 13 is that drug 14 has a limited solubility therein. Wall 11 is formed of a drug release rate controlling material permeable to the passage of drug, as by diffusion, but the rate of passage of the drug through the wall is lower than the rate of passage of drug through the drug carrier. In operation, drug carrier 13 serves as a reservoir by supplying dissolved drug 14 to wall 11 as drug molecules move through the carrier to bathe the inner surface of wall 11. Drug 14 present at the drug carrier/wall interface dissolves in and migrates through wall 11, ultimately reaching the outer surface of wall 11. As drug 14 leaves drug carrier 13, undissolved drug present in reservoir 12 dissolves in carrier 13 to maintain a constant supply of dissolved drug in the carrier for continuously supplying drug at substantially the same rate to wall 11. Wall 11 operates to effectively control the rate of release of drug throughout the useful period of drug release from the device. Thus, a zero order drug release rate can be obtained.

Wall 11 of device 10 is comprised of a drug release rate controlling material permeable to the passage of drug 14, as by diffusion. The material used to make wall 11 can have uniform properties across all its dimension, or it can be microporous, or it can be a material possessing both of these properties. When wall 11 is made from the former material, that is, a material that is substantially imperforate, molecules of drug 14 dissolve in and diffuses through wall 11 by the process of diffusion. When wall 11 is made from the latter material, that is a material having microporous properties, molecules of drug 14 diffuse through a liquid phase, not shown, present in the minute pores, pinholes, or cracks, for example, by absorption of body fluids by a hydrophilic microporous material, by diffusion. When wall 11 is made from a material having both of these properties, drug 14 can be released from device 10 through wall 11 by a concurrent operation of both of these mechanisms, that is, by both diffusion through wall 11 and by diffusion through liquid in the pores of wall 11. In the specification, the permeation mechanism of drug release through the drug release rate controlling material is generically described as " by diffusion" for both types of materials used to fabricate wall 11. The permeability of wall 11 to the diffusion of drug 14 is lower than the permeability of liquid drug carrier 13 to the diffusion of drug 14 and passage through wall 11 thus acts as the rate limiting step for drug release from device 10.

FIG. 3 illustrates another drug delivery device of the invention. In FIG. 3, a drug delivery device 10 designed for administering drug within a body opening is shown positioned in a body having an anal canal 16 located between the buttocks and terminating in an anus 17. Drug delivery device 10 of FIG. 3 is comprised of a wall 11 surrounding a reservoir 12. Reservoir 12 is comprised of a drug carrier 13 containing drug 14. Drug carrier 13 is liquid in nature. Drug carrier 13 is permeable, as by diffusion, or convection or both, to the passage of drug 14, which has limited solubility therein. Wall 11 is made of a drug release controlling material permeable to the passage of drug 14, as by diffusion, and it releases drug from the device at a predetermined, controlled rate within the body. In this device, as with the device discussed above, drug released from carrier 13 is replenished by undissolved drug dissolving in carrier 13 to insure that drug is continuously available to wall 11. Also, in the device of FIG. 3, release of drug through the wall is the rate controlling step for release of drug from this device.

FIG. 4 illustrates another drug delivery device of the invention. FIG. 4 shows a drug delivery device 10 shaped as a vaginal tampon of an elongated, generally cylindrical shape. One end 29 of the tampon is rounded while the opposite end 18 is flat for easy insertion of the drug delivery device into a vagina. The drug delivery tampon is equipped with a manually controlled cord 19 for easily removing the drug delivery tampon from the vagina after the desired degree of medication has been achieved. The drug delivery device 10 is comprised of a reservoir 12 containing a carrier medium 13 with a drug 14 dissolved therein. Carrier medium 13 is a liquid or liquid like solution or medium and drug 14 has limited solubility therein. Carrier medium 13 also contains undissolved drug that will dissolve in the carrier after the drug presently dissolved therein leaves the carrier. Reservoir 12 is confined within a wall member 11 that forms the supportive structure, or main body of device 10. Both the carrier medium and the wall are manufactured from materials that are different and are permeable to the passage of drug, but, the permeability of the carrier to the passage of drug is always higher than the permeability of the wall to the passage of drug. Wall 11 therefore is the rate controlling means for releasing drug from the device. Wall 11 is permeable to the passage of drug as by (1) diffusion through a homogenous wall (2) as by diffusion through micropores in the wall, that is, by diffusive flow through a media contained therein, or (3) both. In actual operation, drug is released from carrier medium 13 that is in intimate contact with wall 11 to the wall and through the wall at a controlled rate of release from the drug delivery device. As drug leaves the carrier, undissolved drug in the reservoir dissolves in the carrier thereby continuously supplying the wall with drug for administration at a zero order rate into the vagina to achieve a desired physiological or pharmacological benefit.

Figure 5:
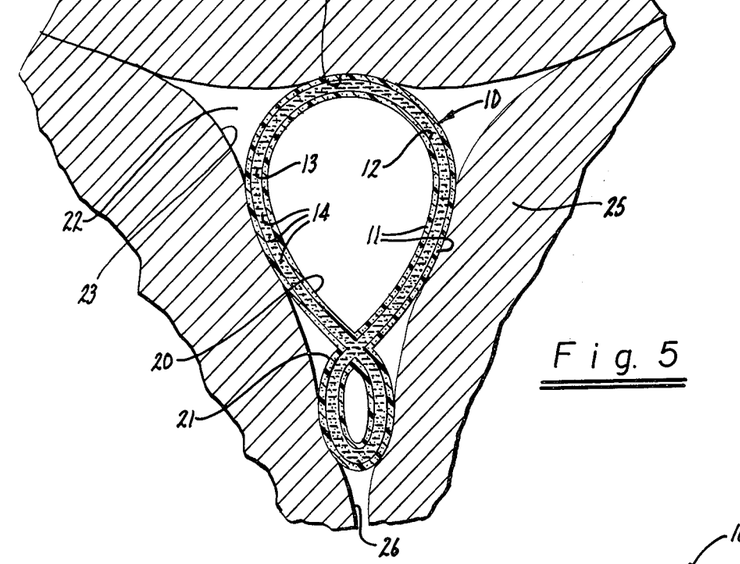
FIG. 5 is a frontal, fragmentary view of a uterine cavity showing a drug releasing intra-uterine device positioned in the cavity.

In FIG. 5 there is graphically depicted an intrauterine contraceptive drug delivery device prepared according to the spirit of the invention. Drug delivery device 10 comprises a wall 11 permeable to the passage of drug, as by diffusion, housing a reservoir 12. Device 10 it will be seen consists of two continuous loops 20 and 21 each having a cross-sectional diameter of about 1.5 to 2.5 cm. Loop 20, the larger of the two loops, is adapted to be located within the uterine cavity 22 and it contacts the sides 23 as well as the fundus uteri 24 of uterus 25. Loop 21, the smaller loop, is positioned in the neck 26 of uterus 25 for assisting in maintaining device 10 within uterus 25. Reservoir 12 is comprised of a carrier medium 13 containing a drug 14. Carrier medium 13 can be a liquid, gel, sol or the like, and a description thereof is presented later in the disclosure. The carrier confined in the reservoir serves several purposes for effectively releasing drug from the device. First, it is permeable to the passage of drug so that drug in the carrier can migrate to wall 11. Secondly, the carrier contacts and bathes the inner surface of wall 11 for facilitating drug transfer from the carrier to the wall so that drug molecules can dissolve in and migrate through the wall to the outer surface thereof. Thirdly, the carrier acts as a constant source of drug and it has a limited, or varying degrees of solubility for drug or a mixture of drugs. The carrier is formulated to contain both dissolved and undissolved drug, and they can be homogenously or heterogenously dissolved and/or dispersed therein. Thus, the carrier is a constant source of drug because, as drug dissolves in the carrier and transfers from the carrier to the wall, undissolved drug dissolves in the carrier to insure a constant and uniform supply of drug until essentially all the drug has been released by the device. This mechanism of continually replenishing the drug enables the device to achieve a uniform, release rate for the device throughout its use.

Wall 11 of the intrauterine contraceptive drug delivery device 10, is formed of a drug release rate controlling material to continuously meter the flow of an effective amount of a drug from the reservoir for release within the uterus. The rate of drug release through the wall is lower than the passage of drug through and/or from the carrier, so that the former is the rate controlling step for drug release from the device. The depicted intrauterine drug delivery device is manufactured in a non-traumatising design for easy insertion into the uterine cavity. The device can be fabricated into assorted sizes, shapes, and thicknesses for adaptation to a wide variety of uteri.

Figures 6, 7, 8:
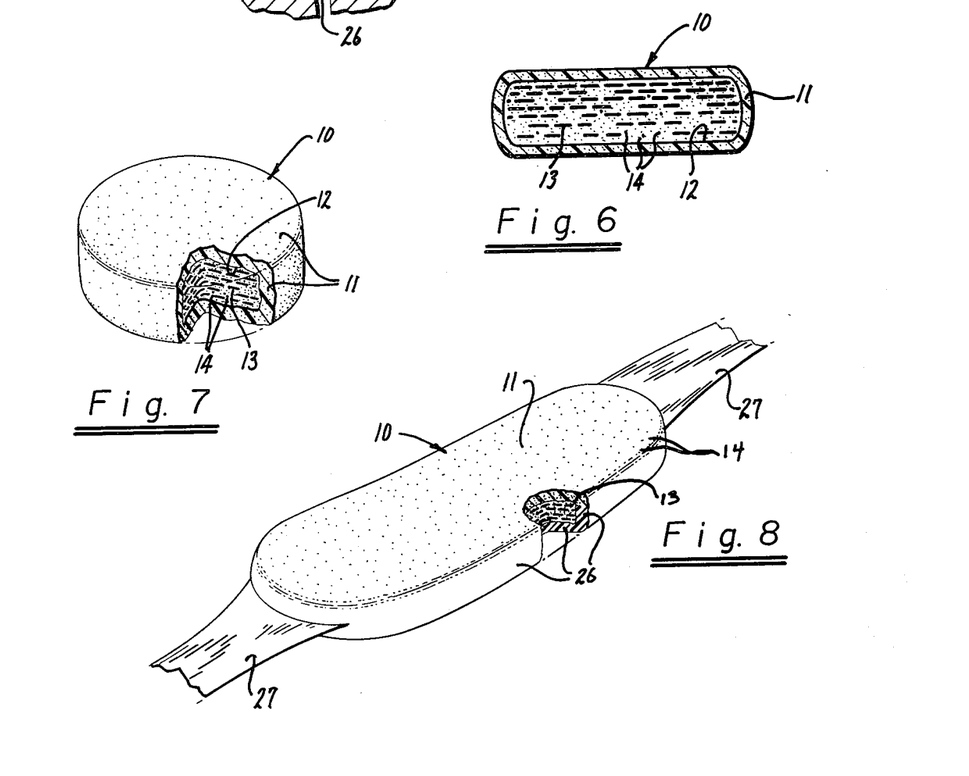
FIG. 6 is a schematic drawing showing a drug delivery implant fabricated in accordance with the invention.
FIG. 7 is a schematic illustration of a drug delivery device shaped as a peroral tablet prepared according to the invention.
FIG. 8 is an isometric view of a catamenial drug delivery device formed of multiple parts, as manufactured according to the spirit of the invention.

In FIG. 6, there is illustrated a drug delivery device 10 for use as a depot implant comprising a wall 11 surrounding a reservoir 12 containing a drug 14 dissolved in a drug solubilizing limited carrier 13. Both the solubilizing limited carrier and the wall are permeable to the passage of drug, as by diffusion, but the rate of drug passage through the wall is lower than through the carrier, so the wall thus acts as the rate limiting barrier for drug release. Drug delivery implant 10 may be of any shape that is adapted for implantation. The implant, as shown, is of cylindrical construction with a view of a longitudinal section through the implant. The implant drug delivery device may be implanted within the body for the purpose of metering to the body at a constant and uniform rate drug for producing any desired medical or pharmaceutical result.

FIG. 7 represents a schematic drawing of a pill or tablet peroral drug delivery device 10 of the invention. This device 10 comprises a wall 11 formed of a material permeable to the passage of drug, as by diffusion, and having enclosed therein a reservoir 12 (shown in opened section) containing a drug 14 in a drug solubilizing limited carrier phase 13. Carrier 13 is fabricated of a non-solidified material permeable to the passage of drug, but the rate of passage of drug is higher in it than is the rate of passage of drug through the wall. The pill or tablet drug delivery devices are suitable for oral administration for continuously metering a flow of an effective amount of drug over a prolonged period of time to the gastrointestinal tract.

FIG. 8 represents a drug delivery device 10 of catamenial shape comprised of a wall surrounding a reservoir in which at least a part of the wall is formed of a drug release rate controlling material permeable to the passage of the drug. Device 10 is comprised of a top wall 11 permeable to the passage of the drug as by diffusion, and it has a shape generally approximating the shape of the exterior surface of the pubic area to which it is to be applied. The remainder of the wall forming the device, side wall 26 and the bottom wall 26, shown in open section, are made from wall forming materials that are impermeable to the passage of drug. Collectively, the top, side and bottom walls surround a reservoir 12, shown in section, that comprises a drug solubilizing limited carrier 13 permeable to the passage of drug 14. Drug 14 in carrier 13 can be in a dissolved state, partially dissolved state or undissolved drug state. Drug 14, shown as dots on the surface of wall 11, is drug that transferred from the carrier to top wall 11, by first dissolving therein and then diffusing through the wall to its exterior surface. The catamenial is provided at its ends with tabs 27 for securing the catamenial in position on the body of the wearer, and also for maintaining it there during delivery of the drug by the drug delivery device. In the device, the diffusion of drug through drug carrier 13 is at a higher rate through the drug release rate controlling material of wall 11 so that passage through the wall member is the drug release rate controlling step for the device for administering drug the wearer.

While the above FIGS. 1 through 8 inclusive are illustrative of various drug delivery devices that can be made according to the invention, it is to be understood that these drug delivery devices are not to be construed as limiting, as the drug delivery devices of the invention can take a wide variety of shapes, sizes and forms for administering the drug at controlled rates to different areas of the body or to different drug receptor sites. For example, the invention includes external and internal drug delivery devices such as skin patches, sublingual or buccal drug delivery devices, peroral devices, arterial devices, nasal and ear drug delivery devices, ocular inserts, suture materials, plastic heart valves, Stan-Edwards heart valves, hip joints, non-thrombogenic hydrocephalus shunt, bone pins, pessaries, prosthesis, artificial glands, cervical rings, troches, intrauterine drug delivery devices of cylindrical, bullet, elliptical, circular, bulbous, loops, bows, and any other geometrical shape that readily lends itself to intrauterine placement such as Birnberg's Bow in U.S. Pat. No. 3,319,625; Comet in U.S. Pat. No. 3,256,878; Majzlin Spring in U.S. Pat. No. 3,397,691; Inhiband in U.S. Pat. No. 3,323,520; Lippes' Loop in U.S. Pat. No. 3,250,271; Bakunin in U.S. Pat. No. 3,405,711; Shamrock in U.S. Pat. No. 3,077,879; the ring with tail; Ota ring, and the like. In each instance, all of the drug delivery devices made according to the invention have a reservoir comprised of a drug and a liquid drug carrier permeable to the passage of drug as by diffusion, or convection and also having limited solubilizing properties for the drug. The reservoir is surrounded by a wall, at least a portion of which is permeable to the passage of the drug by (1) diffusion, or (2) diffusive flow, or (3) by both. The drug rate of release through the wall is lower than the rate of passage through the carrier, so that the drug release rate through the wall is the drug release rate controlling step. Also, all of the drug delivery devices are of appropriate known shapes and sizes for implantation, insertion or positioning in the desired body cavities or on tissues for administering of drug to the body or to a drug receptor site.

DETAILED DESCRIPTION OF THE INNVENTION

In accordance with the practice of the present invention, it has now been found that the drug delivery device of the invention provides many important advantages over previously known drug delivery devices. One advantage of the device is the ease of construction of the drug delivery device by standard manufacturing techniques into devices of various sizes, shapes and forms for delivering drugs to a recipient. A more important advantage of the claimed drug delivery device is to provide a broad range of drug release rates by providing one or more devices having a reservoir, or more than one reservoir in a large multi-purpose device, wherein the reservoir contains a carrier or a mixture of carriers having limited solubility for a drug or a mixture of drugs and where the carrier simultaneously releases drug and dissolves replacement drug to maintain a constant supply of drug for release by the device.

Another important advantage of the invention resides in the drug delivery devices' ability to effectively control the rate of release of the drug from the device by providing a zero order ($dM_t/dt = $ constant) rate of drug release throughout the major portion of the drug release history. Yet another important advantage for the drug delivery device is its ability to administer drug from the device according to a predetermined drug time release pattern, for example, by providing a drug release pattern that is sinusoidal, parabolic, and the like. The drug time release pattern for the device of the invention is obtained by a selection of the drug release parameters, such as, the thickness of the material forming the wall, the nature of the material forming the wall, the nature of the drug carrier in the reservoir, and the kind of drug contained therein.

The above advantages and objects are achieved by the unique construction and operation of the device and its ability to transfer drug to a recipient or to a drug receptor site. In construction, the device can be viewed as a single unit constructed device comprising two structures acting in concert for effective drug administration to a host. One structure pertains to a wall comprising the device and formed of a drug release rate controlling material permeable to the passage of drug and the other structure relates to a reservoir comprising a drug carrier phase formed of a material permeable to the passage of drug. The materials forming the wall and the drug carrier phase comprising the device are chemically and structurally different within a single device and the rate of release of drug through the wall is lower than the rate of passage of drug in the drug carrier phase.

These two structures, comprising the unit drug delivery device, operate to effectively transfer drug from the device by first transferring drug from the carrier to the wall, and secondly, by transferring drug through the wall to a drug recipient. The transfer of drug through the wall can occur by two different processes or drug transfer mechanisms. These drug transfer processes are the diffusion process of a drug through a uniform material and by diffusion of drug through the media present in the micropores of a material, as hereinafter described. Thus, for example, drug can be transferred from the carrier to the wall and then through the wall by diffusion to the drug recipient, or drug can be transferred from the carrier to the wall and then through micropores of the wall by diffusion to the drug recipient. With the devices of this invention, drug can be transferred by using a combination of these mechanisms for transferring drug through the wall. Thus, by fabricating devices having different kinds of walls made from different materials, the device can provide for transfer of drug through the wall by either diffusion in a substantially homogeneous material or by diffusion in a microporous wall. The wall of the drug delivery device is made from a material that has a lower drug release rate than the rate of passage of drug through the drug carrier to ensure that release kinetics of the device are controlled by the release rate of drug through the wall. Thus, by choosing the wall, a zero order release of drug, or a time release pattern of drug to the body or drug receptor site can be achieved.

In the diffusion process, the wall is formed from a drug release rate controlling material that is permeable to the drug to permit passage of the drug by diffusion through the material at predetermined rates. In this process, the drug dissolves and equilibrates in the wall surface, and then diffuses in the direction of lower chemical potential. At the second boundary equilibrium is again established. When the boundary conditions on both sides of the wall are maintained constant, a steady state flux of the drug will be established which can be described by Fick's Law of Diffusion. The rate of passage of drug through the wall material is generally dependent, in the case of diffusion, on the solubility of the drug therein, as well as on the thickness of the material. This means that selection of appropriate materials for fabricating the wall will be dependent on the particular drug to be used. By varying the composition and thickness of the wall, the dosage rates per area of the device can be controlled for this material acts to meter the diffusion of drug from the reservoir. In the devices of this invention, the materials comprising the wall are chemically and/or structurally different than the material comprising the drug carrier of the reservoir. The drug carrier of the reservoir is permeable to the passage of drug, but the rate of diffusion or passage through the wall is lower than the rate of diffusion or passage through the drug carrier, so that the rate of passage of drug through the wall is the rate release controlling step for the device. Thus, through this invention, devices of the same surface area, functioning by diffusion, can give different dosages of a drug by varying the characteristics of wall to give controlled administration of a drug.

In the device of the invention, when the wall is formed from a drug release rate controlling microporous material that is permeable to the drug, the drug transfer mechanism is by diffusive permeation through the micropores at a controlled and predetermined rate. This drug transfer mechanism is diffusion, and it is sometimes referred to as diffusive flow. It is generically referred to in the specification as diffusion. Generally, in this process the rate of permeation or the rate of drug release through the wall is governed by diffusion of the drug through a diffusive medium present in the pores, microholes and cracks of the material forming the wall. The diffusive medium, in one embodiment, is a liquid phase comprised of a solution, a colloidal solution, a suspension, or a sol, and the solution can be polar, semi-polar or non-polar. In these diffusive mediums, the drug can have different degrees of solubility, such as fully soluble, partially soluble and the like, to act in cooperation with the material for achieving a controlled drug release rate.

The diffusive medium can be added to the materal by methods well knon to the art, for example, by immersion of the material in a bath containing the diffusive medium to let the medium partially fill or fully saturate the micropores of the material. Another method for charging the micropores with a diffusive medium is to first add to the reservoir a diffusive medium, or a mixture of diffusive media so that the medium can flow from within the reservoir into the pores and remain therein to permit diffusive flow of later added drug, but not its solubilizing limited carrier, to flow therethrough. The diffusive medium suitable for the immersion purpose are those well known to the art such as wate, glycerin, ethylene glycol, propylene glycol, castor oil, olive oil, alcohols of 2 to 10 carbon atoms, halogenated hydrocarbons having 2 to 20 carbon atoms, aldehydes, and ketones having 4 to 10 carbon atoms, syrups, and the like. Additionally,, the diffusive medium can be emulsifying and suspending agents such as methyl cellulose mixed with water, mixtures of propylene glycol monostearate and oils, gum tragacanth and water, assorted waxes and the like. Representative mediums are set forth in Remington's Pharmaceutical Science, pages 246 to 269 and 1338 to 1380, 1970, published by Mack Publishing Company, Easton, Pa.

The diffusive medium, in another embodiment, can be added to the pores of the material forming the wall by locating the wall in a fluid environment, for example, by contacting the device with a body tissue, for example, the mucous membranes of the anus, mouth or vagina, that can make available its intracellular and/or extra-cellular body fluid for subsequent transfer into the micropores of the wall for functioning as a diffusive medium for the drug. Additionally, the drug delivery device can be positioned in a body fluid, for example, in the fluid present in the stomach of farm animals, the avian cloaca, and the like, for using the fluid contained therein, as above described, as a diffusive medium. In another embodiment, the pores can be filled with plasticizer by immersing the wall in a plasticizer solvent composition, and removing the solvent in vacuo after the filling of the pores. Exemplary plasticizers suitable for employment of the present purpose are the commercially available plasticizers conventionally used for the manufacture of polymeric materials such as diethyl adipate, di-isobutyl adipate, di-n-hexyl adipate, diisooctyl adipate, di-n-hexyl azelate, di-2-ethylhexylazelate, ethylene glycol dibenzoate, acetyl tri-n-butyl citrate, epoxidized soy bean oil, glycerol monoacetate, diethylene glycol dipelargonate, propylene glycol diluarate, isooctyl palmitate, triphenyl phosphate, and the like.

The materials comprising the wall are chemically and/or structurally different than the materials comprising the carrier. Both of the materials are permeable to the passage of drug but the rate of flow through the wall is lower than the rate through the carrier. Thus, the rate of passage of drug through the wall is the rate release controlling step for the device. Generally, for the practice of this invention, the ratio of the drug release rate through the drug carrier of the reservoir to the drug release rate through the wall should be from 100:1 to 2:1 and preferably from 10:1 to 2:1. Of course, the invention is not limited to these release rates as the invention comprises lower or higher release rates from the drug carrier and lower and higher rates through the wall with the release rate of the wall lower than the release rate of the drug carrier. Thus, the invention provides that devices of the same surface area, activated by diffusion, can give different dosages of a drug by varying the characteristics of the wall material to give controlled administration of a drug; Encyclopedia of Polymer Science and Technology, Vol 9, pages 794 to 807, 1968.

For either of the above discussed mechanisms, diffusion through a material, or diffusive flow through a diffusion medium present in a material, the transfer or rate of release of drug through the wall is at a lower rate than the rate of release of drug from the drug carrier of the reservoir for administration to the body or to a drug receptor site. Thus, the passage of the drug through the wall is the drug release rate controlling step for the drug delivery system. In addition, because the reservoir serves to transfer drug molecules to all areas of the wall, the wall of the drug delivery system housing the reservoir remains substantially at the thermodynamic activity corresponding to that of the drug until substantially all of the drug has been released from the reservoir. Ordinarily, one would expect drug migration from the reservoir to cease when sufficient drug has entered the wall to establish an equilibrium; however, when the drug delivery system is in contact with body tissue or fluids, drug molecules are continuously removed from the outer surface of the wall. For optimum results, the rate of release of the drug through the wall should be less than the rate of clearance of migrated drug from the external surface of the device. This ensures that the drug administration rate is dependent on the rate of release of drug through the wall which can be controlled, rather than upon clearance of drug from the device in vivo, which can vary. Thus, in contrast to previously proposed drug delivey devices, the rate of release of the drug from the device of the invention can remain essentially constant until the drug delivery device has substantially completed its useful function.

The term "reservoir" as used in the specification and the accompanying claims generally refers to a "drug carrier" or to a "medium containing drug," that constantly bathes the inner surface of the drug release rate controlling wall and supplies drug thereto. That is, the reservoir is comprised of a drug carrier material containing dissolved drug, and/or undissolved drug, and/or a mixture of both, and it is a material that is permeable to the passage of the drug as by diffusion or convection. The drug carrier medium used for the purpose of the invention is a liquid, and it can be inorganic or organic, and of naturally occurring or synthetic origin. Examples of carriers comprised within the terms liquid are, for example, solutions, immiscible liquids, emulsions, gels, sols, colloids, oils, syrups, suspensions, dispersions, liquid pre-cured polymers, liquid polymers, liquid plasticizers, liquid thixotropic agents, polar solvents, simipolar solvents, nonpolar solvents, liquid-like mediums, mixtures thereof, and the like. Further, for the purpose of this invention, the terms liquid and the examples thereof are deemed as functional equivalents and they can be generically termed "liquid core."

The drug carrier medium comprising the reservoir, also has in addition to the properties described supra, limited solubility for contained drug or for a mixture of drugs. By limited solubility is meant that drug is soluble in given amounts in the carrier, that is, it comprises varying concentration of drug dissolved in the carrier. Essentially, there is also an excess amount of undissolved drug present in the carrier. These varying limited solubility concentrations include solubilities such as, soluble, sparingly soluble, slightly soluble, very slightly soluble, and almost practically insoluble. Generally, on a weight basis at 25°C, the amount of drug dissolved in a carrier that is termed a soluble carrier is about 1 part of drug to about 10 to 25 parts of carrier, the amount of drug dissolved in a carrier that is sparingly soluble for the drug is 1 part of drug to about 25 to 100 parts of carrier, from 100 to 1000 parts of carrier for 1 part of drug when the drug is slightly soluble in the carrier, from 1000 to 10,000 parts of carrier for 1 part of drug when the drug is very slightly soluble in the carrier, and from 10,000 to 15,000 parts of carrier for 1 part of drug in a carrier that is almost practically insoluble for the drug. Hence, the term limited solubility comprises a range of solubility of drug in carrier of 1 part of drug to about 10 to 15,000 parts of carrier on a weight basis at 25°C. The above ranges are set forth to aid in defining the invention, and they should not be considered as limiting as other ranges at higher or lower temperatures are embraced within the above presentation are also included herein. The amount of undissolved drug incorporated in the reservoir will vary depending on the type of drug delivery device, the particular drug, the desired therapeutic effect, and the rate of release of desired drug from the reservoir. That is, there is no critical upper limit on the amount of undissolved drug incorporated in the reservoir, since, it serves as a reserve source of drug for replacing released drug by dissolving in the drug carrier to make drug continually available from the carrier to the wall during the history of the device, or until the device is no longer used. The lower limit will depend on the activity of the particular drug and the time span of its release from the device. Generally, the amount of undissolved drug initially present in the reservoir will range from about 90% by weight to about 99.9% by weight, of the total amount of drug present in the reservoir.

The materials suitable for fabricating the wall of the device are generally those materials capable of forming walls, with or without pores, through which the drug can pass at a controlled rate of release by the process of diffusion or diffusive flow. Such materials are referred to in this specification and the appended claims as "drug release rate controlling materials." Suitable materials for forming the wall are naturally occurring or synthetic materials, preferably materials that are biologically compatible with body fluids, tissues or organs, and essentially insoluble in body fluids with which the device will come in contact. Generally, the use of rapidly dissolving materials or materials highly soluble in body fluids is to be avoided since dissolution of the wall of the device would affect the constancy of the drug release, as well as the capability of the system to remain in place for certain uses for prolonged periods of time.

Exemplary naturally occurring or synthetic materials suitable for fabricating the wall are drug rate release controlling materials such as poly(methylmethracrylate), poly(butylmethacrylate), plasticized or unplasticized poly(vinylchloride), plasticized nylon, plasticized soft nylon, plasticized poly(ethylene terephthalate), natural rubber, poly(isoprene), poly(isobutylene), poly(butadiene), poly(ethylene), poly(tetrafluoroethylene), poly(vinylidene chloride), poly(acrylonitrile), cross-linked poly(vinylpyrrolidone), poly(trifluorochloroethylene), poly (4,4'-isopropylidene diphenylene carbonate), and the like. Also, by way of non-limiting example, copolymers such as ethylene-vinylacetate, vinylidene chloride acrylonitrile, vinyl chloride diethyl fumarate and the like. Examples of other materials include silicone rubbers, especially the medical grade poly(dimethylsiloxanes), and siliconecarbonate copolymers; hydrophilic polymers such as the hydrophilic hydrogels of esters of acrylic and methacrylic acid as described in U.S. Pat. Nos. 2,976,576 and 3,220,960 and Belgian Pat. No. 701,813, modified insoluble collagen, cross-linked polyvinylalcohol, cross-linked partially hydrolyzed polyvinylacetate, and surface treated silicone rubbers as described in U.S. Pat. No. 3,350,216. Other polymeric membranes that are biologically compatible and do not adversely affect the drugs can be used.

Additionally, other materials permeable to the passage of drug suitable for the present purpose include copolymers such as acrylonitrile dithioglycidol, acrylonitrile ethylene oxide, poly(vinyl butyral) comprised of 11% to 45% free hydroxyls, anisotropic permeable microporous membranes of ionically associated polyelectrolytes, the polymers formed by the coprecipitation of a polycation and a polyanion as described in U.S. Pats. Nos. 3,276,589; 3,541,005; 3,541,006; 3,546,142; and the like; treated aliphatic polyamide membranes as in U.S. Pats. Nos. 2,071,253; 2,966,700; 2,999,296; and the like; vinylidene chloride vinyl chloride copolymer 40/60 and 10/90; vinyl chloride acrylonitrile copolymer 80/20, 75/25, 50/50 and the like; vinylidene chloride acrylonitrile copolymer 60/40 and 12/88; water insoluble natural gums, and the like. Also, materials such as regenerated cellulose, cellulose diacetate, cellulose triacetate, regenerated proteins, poly(urethanes), poly(arylenes), poly(carbonates) and the like. Materials having a pore size of several hundredth microns or larger, or down to several angstroms or smaller. For example, the wall can comprise regenerated insoluble, nonerodible cellulose, poly(electrolytes) with a pore size of 7 to 50A, epoxy resins, poly(olefins), poly(vinylchlorides) with a pore size of about 50A or less to 150 microns or larger as conventionally made by leaching out incorporated salts, soap micelles, starch or the like materials to give a microporous membrane. Also, the materials that can be used include those materials having homogeneous properties and microporous properties, such as cross-linked gelatinous membranes; and the like.

The drug carrier used to form the reservoir is comprised of materials of naturally occurring or synthetic origin, of inorganic or organic types that do not adversely affect the drug, or the mixture of drugs contained therein and which are permeable to the passage of drug. Generally, the carrier used does not substantially diffuse from the reservoir, but if the carrier does diffuse from the reservoir, for example if the carrier is an aqueous medium, it would be replaced by a corresponding amount of medium diffusing inward from the exterior of the device when the device is positioned in an aqueous type environment. Representative liquid carriers include ethylene glycol, diethylene glycol, triethylene glycol, propylene glycol, dipropylene glycol, thiodiethylene glycol, ethylene glycol monomethyl ether, ethylene glycol mono-n-butyl ether, ethylene glycol diethyl ether, propylene glycol mon-o-propyl ether, liquid polyethylene glycols having a molecular weight of 200, 300, 400 and 600, 1-3-butylene glycol; solvent system like ethyl acetate-ethyl alcohol-water 10:83:7; isobutyl acetate-isobutyl alcohol-water 24:46:30; mixed binary liquid systems such as methanol:water, ethyl alcohol:water, n-amyl alcohol: ethyl acetate; mixed tertiary liquid systems such as n-butyl acetate-butyl alcohol-water 27:27:46; esters such as liquid methyl propionate, methyl isobutyrate, butyl stearate, dibutyl fumarate; fats and oils of plant, animal and marine origin such as almond oil, babassu oil, corn oil, eucalyptus oil, cottonseed oil, olive oil, palm oil, peanut oil, rapeseed oil, soybean oil, tung oil, whale oil, herring oil; saturated, unsaturated, straight and branched chain liquid fatty acids such as caproic, lauric, arachidic, oleic, linoleic etc.; emulsions of the single phase and two phase types such as oil in water, water in oil, lipophilic-liquid-in-hydrophilic-liquid emulsions with or without suspending ingredients; emulsions of castor oil in aqueous solution of pigskin gelatin, emulsion of gum arabic, water and ethyl cellulose, halogenated hydrocarbons having 2 to 10 carbon atoms, aldehydes and ketones having 4 to 10 carbon atoms, syrups, and the like. Other carriers include silicone oil, medical oil, sterile water; saline; dextrose; dextrose in water or saline; condensation products of castor oil and ethylene oxide combining about 30 to about 35 moles of ethylene oxide per mole of castor oil; liquid glyceryl triester of a lower molecular weight fatty acid; oils with emulsifiers such as mono- or di-glyceride of a fatty acid, or a phosphatide, e.g., lecithin, and the like; aqueous media in the presence of a suspending agent for example, sodium carboxymethylcellulose; sodium alginate; poly(vinylpyrrolidone); and the like, alone, or with suitable dispensing agents such as lecithin; polyoxyethylene stearate; and the like, carriers such as acetamide; N,N-dimethyl acetamide, N-(2-hydroxyethyl) acetamide, and the like. The carrier can also contain adjuvants such as preserving, stabilizing, or wetting agents, and the like.

The rate of release of a drug through various materials can easily be determined by those skilled in the art by standard procedures. In this manner, particular materials used as the device wall as the drug release rate controlling barrier for release of drug from the reservoirs can be selected. Various techniques, such as the transmission method, the sorption desorption method, and the like, can be used as measurers of permeability. One technique that has been found to be eminently well suited is to cast or hot press a film of the material to a thickness in the range of 2 to 60 mils. The film is used as a barrier between a rapidly stirred (e.g., 150 r.p.m.) saturated solution of the drug and a rapidly stirred solvent bath, both maintained at constant temperature (typically 37°C). Samples are periodically withdrawn from the solvent bath and analyzed for drug concentration. By plotting drug concentration in the solvent bath versus time, the permeability constant P of the material is determined by the Fick's First Law of Diffusion.

$$\text{Slope of plot } \frac{Q_1 - Q_2}{t_1 - t_2} = \frac{P \ AC}{h}$$

wherein
$Q_1$ = cumulative amount of drug in solvent in micrograms at $t_1$
$Q_2$ = cumulative amount of drug in solvent in micrograms at $t_2$
$t_1$ = elapsed time to first sample i.e. $Q_1$
$t_2$ = elapsed time to second sample i.e. $Q_2$
A = area of membrane in $cm^2$
C = initial concentration of drug
h = thickness of membrane in cm.
By determining the slope of the plot i.e.

$$\frac{Q_1 - Q_2}{t_1 - t_2}$$

and solving the equation using the known or measured values of A, C, and $h$, the permeability P constant in $cm^2$/time of the material for a given drug is readily determined.

Using the above technique, the permeability constant P of progesterone from isotonic solution through different materials into isotonic solution a 37°C was found to be:

| Membrane | Permeability Constant ($cm^2$/hr) |
|---|---|
| Poly(dimethylsiloxane | $8.0 \times 10^{-2}$ |
| Poly(ethylene) | $4.7 \times 10^{-4}$ |
| Ethylene vinyl acetate copolymer 9% vinyl acetate | $3.8 \times 10^{-3}$ |
| Silicone-polycarbonate copolymer, General Electric Mem 213 | $12.6 \times 10^{-3}$ |

Using the above technique and data to design a device of the invention to release progesterone, one would employ poly(ethylene) as the drug release rate controlling material as the wall if a slow rate of release is desired, and the cured poly(dimethylsiloxane) membrane as the wall if a faster rate of release is desired. Both the poly(ethylene) and the poly(dimethylsiloxane) are commercially available products. The poly(dimethylsiloxane) used above is commercially available Silastic 340 of the Dow Corning Co., and the poly(ethylene) is low density with a melt index of 0.85. These examples and like examples can be used to determine the rate of drug release through different drug release controlling materials by easily ascertained standard techniques known to the art as recorded in J. Pharm. Sci., Vol 52, pages 1145 to 1149, 1963; ibid. Vol. 53, pages 798 to 802, 1964; ibid. Vol 54 pages 1459 to 1464, 1965; ibid. Vol. 55, pages 840 to 843 and 1224 to 1239, 1966; Encyl. Polymer Sci. Technol., Vol 5 and 9, pages 65 to 82 and 794 to 807, 1968; the references cited therein, and the like.

The rate of solubilization, or the rate at which drug will go into solution is quantitatively governed by physico-chemical principles. For an example, a drug particle dispersed in a solvent is surrounded by a thin layer of solvent having a finite thickness $l$ in cm. This layer is considered as an integral part of the drug and it is characteristically referred to as the "stagnant layer." The stagnant layer remains a part of the surface of the drug, moving wherever the drug moves. Using Fick's First Law of Diffusion, the rate of solution is the rate at which a dissolved drug diffuses through the stagnant layer for supplying drug to the reservoir's inner wall. The driving force behind the movement of the drug through the stagnant layer is the difference in concentration of the drug, $C_1$, in the stagnant layer at the surface of the drug and the concentration $C_2$ on the farthest side of the stagnant layer. The difference in concentration $C_1-C_2$ determines the rate at which drug is solubilized in the carrier. Hence, if the carrier on the farthest side contains its optimum concentration because of a low release by the drug release rate controlling wall, the rate of solubilization of new drug will be low. Correspondingly, as drug leaves the carrier new drug is solubilized to establish a steady state within the carrier.

The rate of diffusion of a drug in a solubilizing limited carrier is broadly determined by measuring the rate a drug transfers from one chamber through a sintered glass filter of known pore size and thickness into another chamber and calculating from the obtained data the drug transfer rate. The method is carried out by adding to a first conical flask equipped with a ground glass stopper and a stirring bar, a measured amount of carrier and simultaneously, the drug in the same carrier is added to a second conical flask while keeping the level of the carrier in the two flasks the same. Next, the flasks are stirred, and samples drawn at various time intervals for analysis. The measured rate of drug transport through the sintered glass filter, and the concentration difference of the drug in the two flasks is then calculated. These procedures are known to the art in Proc. Roy. Sci. London, Ser. A, Vol. 148, page 1935; J. Pharm Sci., Vol. 55, pages 1,224 to 1,229, 1966; and references cited therein. The diffusion coefficient of a drug can also be experimentally determined by using the above apparatus or similar apparatus and procedures as described in Diffusion in Solids, Liquids and Gases, by W. Jost, Chapter XI, pages 436 to 488, 1960, Revised Edition, Academic Press Inc., New York.

Also, according to Fick's Law, the rate of drug solution is directly proportional to the area of the drug, A in $cm^2$, as exposed to carrier and inversely proportional to the length of the path through which the dissolved drug molecule must diffuse. Then, the rate of solution of the drug is given by $$R = \frac{DA}{l}(C_1 - C_2)$$

wherein R is the rate of solution, D is a proportionality constant called diffusion coefficient in $cm^2$/sec, and $C_1$, $C_2$, and $l$ are as previously defined. See Remington Pharmaceutical Science, 14th Ed., pages 246 to 269, 1970, Mack Publishing Company.

The solubility of the drug in the drug release rate controlling material comprising the wall of a device broadly is determined by preparing a saturated solution of a given drug and ascertaining, by analysis, the amount present in a definite area of the material. For example, the solubility of the drug in the wall is determined by first equilibrating the wall material with a saturated solution of the drug at a known temperature, for example 37°C, or with a pure liquid drug, if the drug is a liquid at 37°C. Next, drug is desorbed from the saturated wall material with a suitable solvent for the drug. The resultant solution for the drug then is analyzed by standard techniques such as ultraviolet, visible spectrophotometry, refractive index, polarography, electrical conductivity and the like, and calculating from the data the concentration, or solubility of the drug in the material.

The solubility of a drug in a liquid core carrier can be determined by various art known techniques. One method consists in preparing a solution, i.e. a carrier, of the given drug and ascertaining by analysis the amount of drug present in a definite quantity of the carrier. A simple apparatus for this purpose consists of a test tube of medium size fastened upright in a water bath maintained at constant temperature. The carrier and drug are placed in the tube and stirred by means of a motor driven rotating glass spiral. After a given period of stirring, a definite weight of the carrier is analyzed and the stirring continued for an additional period of time. If the analysis shows no increase of dissolved substance after the second period of stirring, the results are taken as the degree of solubility of the drug in the carrier. Numerous other methods are available for the determination of the degree of solubility of a drug in a liquid carrier. Typical methods used for the measurement of solubility are chemical analysis, measurement of density, refractive index, electrical conductivity, and the like. Details of various methods for determining solubilities are described in United States Public Health Service Bulletin No. 67 of the Hygienic Laboratory; Encyclopedia of Science and Technology, Vol 12, pages 542 to 556, 1971 McGraw-Hill, Inc; Encyclopaedic Dictionary of Physics, Vol 6; pages 545 to 557, 1962, Pergamon Press, Inc; and the like.

Using the procedures and formulas above described, one skilled in the art can design a drug delivery device according to the invention by ascertaining the properties of the wall and carrier forming material and then fabricating a drug delivery device by selecting a carrier in which the drug has limited solubility and which is permeable to the drug but at a lower rate than the permeability of the wall. For example, by using the permeability coefficient, which is determined by using the procedures and formulas, and which permeability coefficient is defined as the product of the diffusion coefficient, $D_w$, of the drug in the wall, and a distribution coefficient, K, which is a ratio of the solubility of the drug in the wall to the solubility of the drug in the saturated solution, the selection of materials for forming the wall and the carrier can be made for making a device according to the invention. For purposes of comparing the permeability of the wall to that of the carrier, it is convenient to define the permeability as follows: $P_w = PC = D_w S_w$ wherein P, C and $D_w$ have the meaning as above described and $S_w$ is the solubility of the drug in the wall. The permeability of the wall carrier to the drug can similarly be defined as $P_c = D_c S_c$ wherein $D_c$ and $S_c$ are the diffusion coefficient and the solubility of the drug in the liquid core carrier. The solubility, $S_c$, can be determined by methods previously cited. The diffusion coefficients of drug in liquid carriers will be in the range of $10^{-6}$ to $10^{-5}$ cm$^2$/sec. The diffusion coefficient of the drug in the wall will be in the range of $10^{-10}$ to $10^{-8}$ cm$^2$/sec. Thus, a selection of carrier materials such that $P_c > P_w$, preferably $P_c \geq 5 P_w$, is ascertained for preparing a drug delivery device. The symbol ">" means greater than and the symbol "$\geq$" means greater than or equal to.

By using the above described techniques, the degree of solubility of various drugs in select carriers is ascertained as follows: N-methyl-N-2-propylbenzlamine hydrochloride very slightly soluble in water; isoamyl nitrite miscible with alcohol; pentaerythriol tetranitrate diluted with lactose slightly soluble in alcohol; isoxsuprine hydrochloride slightly soluble in mixture of water and alcohol; levonordefrin slightly soluble in ketones; pralidoxine chloride sparingly soluble in methanol; phenoxybenzamine hydrochloride sparingly soluble in water; bendroflumethiazide practically insoluble in water; methyclothiazide sparingly soluble in methanol, slightly soluble in alcohol and very slightly soluble in water and isopropyl alcohol; triamterene sparingly soluble in 2-methoxyethanol and very slightly soluble in dilute mineral acids; ergotamine slightly soluble in water in presence of slight excess of tartaric acid; desoxycorticosterone acetate sparingly soluble in dioxane and slightly soluble in vegetable oils; estradiol sparingly soluble in vegetable oils; estradiol valerate sparingly soluble in sesame oil and peanut oil; dienestrol slightly soluble in fatty oils; ethynodiol diacetate sparingly soluble in fixed oils; progesterone sparingly soluble in vegetable oils; nikethamide miscible with water; flurothyl miscible with propylene glycol; and the like.

In the specification and the accompanying claims, the term, "drug", broadly includes physiologically or pharmacologically active substances for producing a localized or systemic effect or effects in mammals including humans and primates; avians such as chicken and turkeys; valuable domestic household, sport or farm animals such as horses, dogs, cats, cattle, sheep and the like; or for administering to laboratory animals such as mice, monkeys, rats, guinea pigs; and the like. That is, the novel drug delivery device can be used for administering drugs that are physiologically or pharmacologically active at a point in near relation to the drug delivery device, or, for administering a systemically active drug which will produce a physiological or pharmacological response at a site remote from the point of application of the drug delivery device. The active drugs that can be administered by the drug delivery device of the invention include, without limitation: for example, drugs acting on the central nervous system such as, hypnotics and sedatives such as pentobarbital sodium, phenobarbital, secobarbital, thiopental, etc.; heterocyclic hypnotics such as dioxopiperidines, and glutarimides; hypnotics and sedatives such as amides and ureas exemplified by diethylisovaleramide and α-bromoisovaleryl urea and the like; hypnotics and sedative alcohols such as carbomal, naphthoxyethanol, methylparaphenol and the like; and hypnotic and sedative urethans, disulfanes and the like; psychic energizers such as isocarboxazid, nialamide, phenelzine, imipramine, tranylcypromine, pargylene and the like; tranquilizers such as chloropromazine, promazine, fluphenazine reserpine, deserpidine, meprobamate, benzodiazepines such as chlordiazepoxide and the like; anticonvulsants such as primidone, diphenylhydantoin, ethotoin, pheneturide, ethosuximide and the like; muscle relaxants and anti-parkinson agents such as mephenesin, methocarbomal, trihexylphenidyl, biperiden, levo-dopa, also known as L-dopa and L-$\beta$-3-4-dihydroxyphenylalanine, and the like; analgesics such as morphine, codeine, meperidine, nalorphine and the like; anti-pyretics and anti-inflammatory agents such as aspirin, salicylamide, sodium salicylamide and the like; local anesthetics such as procaine, lidocaine, naepaine, piperocaine, tetracaine, dibucaine and the like; antispasmodics and antiulcer agents such as atropine, scopolamine, methscopolamine oxyphenonium, papaverine, prostaglandins such as $PGE_1$, $PGE_2$, $PGF_{1\alpha}$, $PGF_{2\alpha}$, PGA and the like; anti-microbials such as penicillin, tetracycline, oxytetracycline, chlorotetracycline, chloramphenicol, sulfonamides and the like; antimalarials such as 4-aminoquinolines, 8-aminoquinolines and pyrimethamine; hormonal agents such as prednisolone, cortisone, cortisol and triamcinolone; androgenic steroids, for example, methyltestosterone, fluoximesterone and the like; estrogenic steroids, for example, 17$\beta$-estradiol and ethinyl estradiol; progestational steroids, for example 17$\alpha$-hydroxyprogesterone acetate, 19-nor-progesterone, norethindrone and the like; sympathomimetic drugs such as epinephrine, amphetamine, ephedrine, norephinephrine and the like; cardiovascular drugs, for example, procainamide, amyl nitrate, nitroglycerin, dipyridamole, sodium nitrate, mannitol nitrate and the like; diuretics, for example, chlorothiazide, flumethiazide and the like; antiparasitic agents such as bephenium hydroxynaphthoate and dichlorophen, dapsone and the like; neoplastic agents such as mechlorethamine, uracil mustard, 5-fluorouracil, 6-thioguanine, procarbazine and the like; hypoglycemic drugs such as insulins, protamine zinc insulin suspension, globin zinc insulin, isophane insulin suspension, and other art known extended insulin suspensions, sulfonylureas such as tolbutamide, acetohexamide, tolazamide, and chlorpropamide, the biguanides and the like; nutritional agents such as vitamins, essential amino acids, essential fats and the like; and other physiologically or pharmacologically active agents. Also, the drugs can be present as the pharmacologically acceptable derivatives, such as ethers, esters, amides, acetals, etc. that lend themselves to passage into the circulatory system. For highly water soluble drugs, it is preferable that the wall or the reservoir, or both be formed from a material that is substantially impermeable to water to essentially prevent dilution of the drug by absorption of body fluids into the device with an accompanying decrease in drug release rate. These derivatives can be prepared by art known techniques and then used in the practice of the invention. Of course, the drug derivative should be such as to convert to the active drug within the body through the action of body enzymes assisted transformation, pH, specific organ activities, and the like.

The amount of drug present in the reservoir, whether dissolved, partially dissolved or undissolved, is generally non-limited and it is an amount equal to or larger than the amount of a drug that on its release from the device is effective for bringing about the drug's physiological or pharmacological local or systemic effects. For example, the amount of drug present in the reservoir of a drug delivery device when the device is used for a period of time to achieve local or systemic effect for various drugs, such as 11-desmethoxyreserpine is for about 5 to 40 mg in the reservoir; for acetophenazine an amount in the reservoir of 100 to 200 mg; for methoxypromazine about 600 to 750 mg in the reservoir; for emcylamate a reservoir amount of 1.5 to 2.0 gm; for phenylglycodol a reservoir amount of 1.5 to 1.9 gm; about 160 to 250 mg of butabarbital in the reservoir; about 150 to 170 mg of chlorodiazepoxide; from 0.5 to 1.2 gm of methsuximide; from 0.7 to 1.9 gm of ethosuximide; from 20 to 40 mg of hydrolazine; about 50 to 100 mg of totazoline; and the like. Generally, the drug delivery devices made according to the invention can contain from about 250 nanograms to 50 grams of drug for releasing it at a controlled rate of from about 25 nanograms to about 25 grams of drug or larger amounts per day. Of course, other devices containing different amounts of drug for use for different time periods such as week, month and year are also readily made by the invention.

It will be appreciated by those versed in the art that the unique drug delivery device of this invention can provide for the programmed delivery of drug at a rate of delivery characterized by a zero order time dependence for prolonged period of time; and, that the device therefore lends itself to administering an effective amount of drug needed for a therapeutic effect while essentially avoiding the presence of excessive amount of drug at the needed biological site. By a prolonged period of time is meant, as used herein, periods that embrace the time needed for a fast acting drug to effect its end up to periods that embrace the continual, uninterrupted, repititious time of a long term drug delivery device. For example, the prolonged time can be 1 hour or more for drugs, like local anesthetics, analgesics, prostaglandins or the like, that are effective in nanogram and milligram amounts, or the like, to three years or longer for steriods released within the uterine cavity. Other examples include wherein the amount of drug in the reservoir can be 100 to 300 mg of thiopropzate for releasing 15 to 30 mg over a 24 hour period; 200 to 400 mg in the reservoir of phenyltoloxamine for a release of 150 to 200 mg per day; 100 to 200 mg of papaverine in the reservoir for a topical release 30 to 75 mg over a 24 hour period; 2.5 g to 4.0 g of mephenoxalone for a release of 1.0 to 1.5 g per day; 15 to 25 mg of tranylcypromane for a release of 10 to 15 mg as the standard dose; 1 to 2 gm of trimethadione present in the reservoir for a release administration of 0.5 to 1.0 g per day; prostaglandins for example $PGE_1$, $PGE_2$, $PGA_1$, $PGF_2$ in amounts of 0.5 mg to 10 mg for release of 1 ng to 100 ng and the like; for progestogen or progesterone the administration in the uterus of 10 to 200 $\mu$g per day for release for 1 year to 3 years as an anti-fertility agent in a mature, child-bearing woman; an oral device administering 300 mg to 600 mg per day of analgesic acetaminophen to a 60 to 70 kg adult male; and the like.

The reservoir comprising the liquid core and the drug is fabricated by standard techniques. For example, in one embodiment the liquid can be mixed with the drug in solid, semi-solid, or liquid forms at the time of mixing, and then distributed therethrough by conventional methods, such as ballmilling, calendering, stirring, shaking, roll-milling, and the like. The liquid core is then charged into a drug release rate controlling material and sealed therein. In another embodiment the liquid core and the drug are mixed and then charged into a highly permeable tube that is positioned within a drug release rate controlling material. Alternatively, the tube can be coated with the release rate material, or a prepolymer can be cast around the tube and finally cured into a drug release rate controlling material. The wall material forming the device and having the reservoir contained therein can be formed to a given drug design by molding, casting, pressing, extruding, drawing, rotational molding, compression and transfer molding, or like standard processes of manufacture. Also, depending on the material used to form the wall, a monomers may be cured at this stage of manufacture. The ability to design and shape the wall into tubes, rods, discs, films, rings and other highly reproducible shapes of controllable composition, readily results in fabrication of drug delivery devices with controlled characteristics and thus overcomes a significant disadvantage of previously described devices. Other standard procedures, as described in Modern Plastics Encyclopedia, Vol. 46, pages 62 to 70, 1969, well known to those skilled in the art can be used to fabricate the drug delivery device of the invention.

The following examples are merely illustrative of the present invention and they should not be considered as limiting the scope of the invention in any way, as these examples and other equivalents thereof will become apparent to those versed in the art in the light of the present disclosure, drawings and the accompanying claims.

EXAMPLE 1

A drug delivery device comprising a reservoir containing a drug and a liquid core surrounded by a drug release rate controlling wall permeable to the passage of drug is manufactured as follows: first, a reservoir comprised of a liquid dispersion consisting of 11% by weight of progesterone and 10% by weight of barium sulfate in a mixture consisting of 3 parts by weight of Dow-Corning Silastic 382 elastomer resin liquid silicone oil and 1 part by weight of Dow-Corning 360 medical grade silicone oil are thoroughly mixed in a standard laboratory v-blender to yield a liquid dispersion. The progesterone is sparingly soluble in the liquid dispersion. Next, an aliquot of the liquid dispersion is injected into a section of medical grade polyethylene tubing having an outside diameter of 0.110 inches and an inside diameter of 0.070 inches and the end of the tubing heat sealed with a standard, hand heater. The filled polyethylene tubing, about 10 cm in length, then is placed into the lower half of a two piece triangular shaped mold, the upper half is placed thereon, and the mold electrically heated to yield a triangular shaped drug delivery device. The device will release about 25 to 30 micrograms of progesterone per day for controlling fertility in an adult woman.

EXAMPLE 2

A drug delivery implant device comprised of a drug release rate controlling wall permeable to the passage of drug and surrounding a reservoir comprised of a drug and a liquid core for releasing progesterone for cattle is manufactured as follows: a liquid dispersion drug carrier is prepared by intimately contacting and blending in a rotating mill 25% by weight of progesterone and 10% by weight of barium sulfate with a mixture comprising 3 parts by weight of Dow-Corning 382 elastomer resin, low molecular weight prepolymer liquid silicone and 1 part by weight of Dow-Corning 360 medical fluid silicone oil to yield a liquid dispersion. The liquid dispersion is permeable to the drug and the drug is sparingly soluble therein. Next, the liquid dispersion is injected into a length of ethylene vinyl acetate copolymer tubing comprised of 9% by weight of vinyl acetate and having an inside diameter of 0.075 inches and an outside diameter of 0.110 inches. The ends of the tubing are heat sealed and the tubing is then formed into an open ring by means of a heated mold. The device releases 90 to 100 micrograms of progesterone per day.

EXAMPLE 3

Following the procedure set forth in Example 1, a drug reservoir comprised of a liquid core containing aqueous poly(vinyl pyrrolidone) and progesterone housed within a poly(ethylene) barrier is prepared by generally following the example. The drug is sparingly soluble in the aqueous poly(vinyl pyrrolidone) and both the poly(vinyl pyrrolidone) and the poly(ethylene) are permeable to the passage of the steroid, but the rate of passage is lower for the poly(ethylene). The poly(ethylene) barrier has a thickness of 50 microns, and it releases about 33 micrograms per square centimeter per day of progesterone to a drug receptor site.

EXAMPLE 4

A drug delivery device shaped like an elongated, end-tapered tablet and comprised of a liquid carrier of aqueous carboxymethylcellulose containing progesterone laminated between two poly(ethylene) sheets, sealed at their perimeters, and having a thickness of 50 microns is prepared according to the procedure of Example 1. The steroid, in this device, is sparingly soluble in the carrier, and both the carrier and the poly(ethylene) are permeable to the passage of the steroid, with the rate of passage for the former higher than the rate of passage of the latter. The use of this device results in a controlled, rate of release of progesterone over a prolonged period of about 1 year at the rate of 33 micrograms per sq. cm. per day.

EXAMPLE 5

Repeating the general procedure as described in Example 1, a drug delivery device is made of a drug permeable, release rate controlling wall of ethylene vinylacetate copolymer of 91% ethylene and 9% vinyl acetate of about 50 microns thick and surrounding a reservoir comprised of progesterone in water is made by substituting the ingredients of this example for those set forth above. A drug delivery device made according to this procedure will release about 230 micrograms of progesterone per sq. cm. per day.

EXAMPLE 6

A drug delivery device suitable for use as a tampon is comprised of an insoluble, drug permeable, ethylene vinyl acetate elastomer wall shaped as an elongated cylinder defining a discrete, hollow reservoir. The reservoir is filled with hydrocortisone in a very slightly soluble carrier. The carrier is prepared by adding hydrocortisone to water lightly charged with methyl cellulose. After the reservoir is filled, the wall is closed. Positioning of the drug delivery device within the cavity results in the metering of hydrocortisone through the copolymer wall to the environment at a controlled rate during the used period of the device.

EXAMPLES 7 TO 14

Other drug delivery devices made according to the procedure set forth in the disclosure and the previous examples include the following drug delivery devices containing 10 to 90% of drug in a carrier phase within a drug delivery device: comprising phenazocine hydrochloride in sparingly soluble water carrier encased within plasticized poly(vinyl chloride); an intrauterine drug delivery device comprised of the drug progesterone, the carrier water in the reservoir with a wall comprised of ethylene vinyl acetate copolymer wherein the vinyl acetate is 33% of the copolymer; the device as just described wherein the wall is formed from finely ground radiation cross-linked poly(cis-1,4-polyisoprene); and ocular insert drug delivery device consisting of pilocarpine in a sparingly soluble mixture enclosed in ethylene vinyl acetate copolymer comprising 18% vinyl acetate; a drug delivery device comprising a non-thrombogenic hydrocephalus shunt consisting of a heparin in a solubilizing limited carrier phase and surrounded with a wall of insoluble polyester; a drug delivery device for oral use shaped as a drug administering elastic rubber band wherein the reservoir contains a drug in a sparingly soluble carrier surrounded with poly(ethylene); a drug delivery device designed as a Stan-Edwards heart valve comprising high density poly(ethylene) around a drug reservoir; and, a drug delivery device manufactured as a suture comprising a wall formed of a polyamide encapsulated around a reservoir of drug and carrier.

It will be understood to those versed in the art in the light of the present specification, drawings and accompanying claims that the invention makes available to the art both a novel and useful drug delivery device for administering a drug to produce a local or systemic physiologic or pharmacologic effect; as, the rate of release of drug administered from the device can be controlled to produce these effects, while simultaneously lessening or overcomimg the undesirable effects frequently associated with the administration of drugs by prior art methods. It will be further understood to those versed in the art that many different embodiments of this invention can be made without departing from the spirit and the scope of the invention. Accordingly, it is to be understood that the invention is not to be construed as limited, but it embraces all equivalents inherent therein.

I claim:

1. A delivery device for the controlled and continuous administration of drug to a body site environment over a prolonged period of time, said device comprising:
   a. a means for containing and releasing the drug at a controlled rate comprising a reservoir containing a dissolved drug portion and an undissolved replacement drug portion in a liquid carrier material permeable to the passage of the drug therethrough, said drug having limited solubility in said liquid; the replacement drug portion being present in an amount in excess of its solubility in the carrier material and in an amount sufficient to maintain the amount of the dissolved drug portion substantially constant during said prolonged period of time, said means further comprising:
   b. a shaped wall that surrounds the reservoir and is characterized by being insoluble in body fluid, maintaining its integrity during said prolonged period of time, and by being formed at least in part of a substantially homogeneous drug release rate controlling material permeable to the passage of the drug but having a lower permeability to the drug than the permeability of the liquid carrier material to the drug;
   c. so that the device when placed at the body site, continuously releases drug from the reservoir to the body site at a physiologically or pharmacologically effective controlled rate by metered passage through the wall, the dissolved drug so released being replaced by the continuous dissolving of replacement drug in the carrier material so as to substantially maintain the amount of dissolved drug in the reservoir substantially constant during said prolonged period of time.

2. A delivery device in accordance with claim 1 wherein the drug release rate controlling material is a natural or synthetic organic polymer free from silicon atoms in the polymeric network.

3. A delivery device in accordance with claim 1 wherein the wall is permeable to the passage of drug by diffusion.

4. A delivery device in accordance with claim 3 wherein the cumulative amount of dissolved drug and undissolved drug contained in the liquid carrier material is in an amount to provide a complete dosage regimen for a living organism for a period of time in an amount of at least one month.

5. A delivery device in accordance with claim 1 wherein the drug release rate controlling material is ethylene-vinyl acetate copolymer.

6. A delivery device in accordance with claim 1 wherein the permeability of the liquid carrier material to drug is from 2 to 100 times the permeability of the drug release rate controlling material to drug.

7. A delivery device in accordance with claim 1 wherein the rate of controlled and continuous release from the device is substantially independent of time.

8. A delivery device in accordance with claim 1 wherein drug in the reservoir is maintained at the same thermodynamic activity until substantially all of the drug has been transferred from the reservoir to the exterior of the device.

9. A delivery device in accordance with claim 1 wherein the drug is soluble in the liquid carrier material in an amount of one part of drug to about 10 to 15,000 parts of liquid carrier material at 25°C.

10. A delivery device in accordance with claim 1 wherein liquid carrier material is permeable to the passage of drug by diffusion.

11. A delivery device in accordance with claim 1 wherein the prolonged period of time is at least a period of 1 month.

12. A delivery device in accordance with claim 1 wherein the device is an intrauterine device, said environment of use being the uterus of a female mammal.

13. A delivery device in accordance with claim 12 wherein the drug is comprised of progesterone, the liquid carrier material is an oil, and the drug release rate controlling medium material is ethylene-vinyl acetate copolymer.

14. A delivery device in accordance with claim 1 wherein the permeability of said drug release rate controlling material to said drug is such that the rate of flow of drug from the reservoir is less than the rate of clearance of migrated drug from the external surface of the device when the device is in contact with body tissues or fluids.

15. A delivery device in accordance with claim 1 wherein the drug is soluble in the liquid carrier material in an amount of one part of drug to 100 to 1000 parts of liquid carrier material at 25°C.

16. A delivery device in accordance with claim 13 wherein the prolonged period of time is one to three years and the total amount of progesterone present in said reservoir is sufficient to administer from 10 to 200 μg per day during said period.

17. A delivery device in accordance with claim 1 wherein the materials comprising the reservoir and the wall are such that said release and dissolving occurs without substantial absorption of fluid from the environment into the device.

18. A delivery device in accordance with claim 1 wherein the drug release rate controlling material is substantially impermeable to fluids of said environment.

19. A delivery device in accordance with claim 16 wherein the materials comprising the reservoir and the wall are such that said release and dissolving occurs without substantial absorption of body fluids.

20. A delivery device in accordance with claim 16 wherein the drug release rate controlling material is substantially impermeable to body fluids.

* * * * *